United States Patent [19]

Giraudon et al.

[11] Patent Number: 4,579,853

[45] Date of Patent: Apr. 1, 1986

[54] 2-CYANO-IMIDAZOPYRIDINE DERIVATIVES AND THEIR USE AS FUNGICIDES

[75] Inventors: Raymond Giraudon, Lesigny; Georges Santini, Thiais, both of France

[73] Assignee: Rhone-Poulenc Agrochimie, Lyons, France

[21] Appl. No.: 590,454

[22] Filed: Mar. 16, 1984

[30] Foreign Application Priority Data

Mar. 16, 1983 [FR] France ................ 83 04531

[51] Int. Cl.$^4$ .............. A01N 43/90; C07D 471/04
[52] U.S. Cl. .......................... 514/303; 546/118
[58] Field of Search ............ 546/118; 424/256; 514/303

[56] References Cited

U.S. PATENT DOCUMENTS 3,459,759 8/1969 Röchling et al. ............ 260/296

FOREIGN PATENT DOCUMENTS 1213654 11/1970 United Kingdom ............ 546/118

OTHER PUBLICATIONS

Aldrich Catalogue—Aldrich Chem. Co., Milwaukee, Wi., (1982–1983), pp. 374 and 375.

*Primary Examiner*—Richard A. Schwartz
*Assistant Examiner*—Bernard I. Dentz
*Attorney, Agent, or Firm*—Burns, Doane, Swecker & Mathis

[57] ABSTRACT

The invention relates to new 2-cyanoimidazopyridine derivatives.

These compounds have the formula (I):

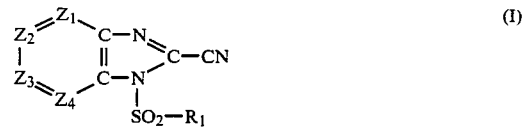

in which: $R_1$ represents an optionally halogenated lower alkyl or cycloalkyl radical or an amino radical optionally substituted by one or two lower alkyl radicals, one of the groups $Z_1$, $Z_2$, $Z_3$ and $Z_4$ represents a nitrogen atom and the others are chosen independently from the CH group and CR groups in which R represents a halogen atom or an optionally substituted lower alkyl, optionally substituted lower alkoxy, optionally substituted lower alkylthio, nitro or cyano radical.

They can be used in agriculture for combating phytopathogenic fungi.

37 Claims, No Drawings

2-CYANO-IMIDAZOPYRIDINE DERIVATIVES AND THEIR USE AS FUNGICIDES

The present patent application relates to new 2-cyano-imidazopyridine derivatives and to the preparation of these compounds. It also relates to pesticidal compositions, in particular fungicidal compositions, containing at least one of these compounds as the active ingredient, and to fungicidal treatments carried out by means of these new compounds.

Finally, it relates to certain compounds, as new products, which can be used for carrying out the above-mentioned preparation process.

The new 2-cyano-imidazopyridine derivatives according to the invention have the general formula (I):

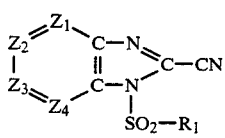
(I)

in which: $R_1$ represents a lower alkyl or cycloalkyl radical optionally substituted by one or more halogen atoms (such as, e.g., the methyl, ethyl, isopropyl and trichloromethyl radicals and the like); or an amino radical which is optionally substituted by one or two identical or different lower alkyl radicals (e.g. the dimethylamino, diethylamino or methylethylamino radicals and the like), one of the groups $Z_1$, $Z_2$, $Z_3$ and $Z_4$ represents a nitrogen atom and the others are chosen independently from the CH group and CR groups in which R represents a halogen atom, a nitro group, a cyano group or a lower alkyl, alkoxy or alkylthio group which may optionally be substituted by one or more halogen atoms, it being understood that the substituents R can be identical or different.

In the sense of the present text, the adjective "lower" when applied to an organic radical means that this radical contains not more than six carbon atoms.

Of the compounds of the formula (I), the present patent application more particularly relates to compounds in which: $R_1$ has the same meaning as in formula (I), and preferably represents a dialkylamino radical containing 2 to 4 carbon atoms, and the groups $Z_1$, $Z_2$, $Z_3$ and $Z_4$ respectively have the following meanings: the group $Z_1$ or the group $Z_4$ represents a nitrogen atom, one to three of the other groups (i.e. one to three of the groups $Z_2$, $Z_3$ and $Z_4$, if $Z_1$ represents a nitrogen atom, or one to three of the groups $Z_1$, $Z_2$ and $Z_3$, if $Z_4$ represents a nitrogen atom) represent the CH group, and the remaining groups represent the CR group, in which R has the same meaning as in formula (I). R preferably represents a halogen atom or an alkyl radical which contains 1 to 3 carbon atoms and is optionally substituted by one or more halogen atoms (such as the trifluoromethyl radical) or a nitro radical or a cyano radical.

Depending on whether $Z_4$ or $Z_1$ represents a nitrogen atom, the invention particularly relates to compounds of, respectively, either the formula (I a) or the formula (I b) below:

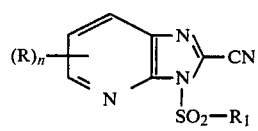
(I a)

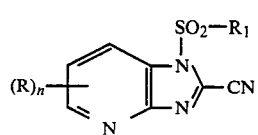
(I b)

in which R and $R_1$ have the same meaning as in formula (I) and n is equal to 0, 1 or 2, it being understood that if n is equal to 2, the substituents R can be identical or different.

Preferably, the substituents present in formulae (I a) and (I b) are as defined below: $R_1$ represents a dialkylamino radical containing 2 to 4 carbon atoms, n is equal to 0, 1 or 2 and R represents a halogen atom or an alkyl radical which contains 1 to 3 carbon atoms and is optionally substituted by one or more halogen atoms or a nitro radical or a cyano radical, it being understood that if n is equal to 2, the substituents R can be identical or different.

The compounds of the formula (I) generally have an excellent fungicidal activity against various families of phytopathogenic fungi, in particular against phycomycetes, such as potato and tomato blight (*Phytophthora infestans*), blue mould of tobacco (*Peronospora tabacina*) and downy mildew of vine (*Plasmopara viticola*). These properties will be described in more detail in the biological examples illustrating the present patent application.

Certain imidazopyridine derivatives have already been described in the literature. Thus, British Patent Specification No. 1,213,654 describes a very comprehensive family of imidazopyridines which are substituted on the carbon atom in position 2 by a trifluoromethyl or pentafluoroethyl radical, and it indicates that these compounds can be used chiefly as herbicides, that they can also be used as insecticides, mollusquicides or fungicides, and that certain of them moreover exhibit an activity against flies, mosquitoes and spiders.

The compounds claimed in the present patent application are distinct from those described in this patent specification No. 1,213,654. Their excellent fungicidal properties were not obvious from this prior art.

The invention furthermore relates to a process for the preparation of the compounds of the formula (I).

This process comprises reacting the 2-cyanoimidazopyridine of the formula (II)

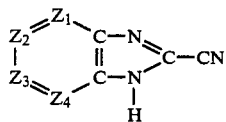
(II)

in which $Z_1$, $Z_2$, $Z_3$ and $Z_4$ have the same meaning as in formula (I), or a salt of this compound (II), advantageously an alkali metal, alkaline earth metal or optionally substituted ammonium salt, with a halide of the formula (III)

 (III)

in which $R_1$ has the same meaning as in formula (I) and X represents a halogen atom, preferably a chlorine atom.

The reaction of the 2-cyano-imidazopyridine (II) with the halide (III) is advantageously carried out in the presence of an acid acceptor, in an anhydrous or nonanhydrous medium, in a solvent which is inert under the reaction conditions, in general at the boiling point of the solvent.

Acid acceptors which may be mentioned are mineral bases, such as, e.g., sodium hydroxide or potassium hydroxide or alkali metal or alkaline earth metal carbonates, or nitrogen bases, such as triethylamine. Solvents which are advantageously used are polar aprotic solvents, such as, e.g., dimethylformamide, dimethylacetamide, dimethylsulphoxide, acetone, methyl ethyl ketone, acetonitrile and N-methylpyrrolidone. If desired, this reaction can be carried out in the presence of an appropriate catalyst. As catalysts which can be used, there may be mentioned phase transfer catalysts, such as, e.g., quaternary ammonium derivatives.

The reaction of the salt (an alkali metal, alkaline earth metal or optionally substituted ammonium salt) of the 2-cyano-imidazopyridine (II) with the halide (III) does not require the presence of an acid acceptor. It is advantageously carried out in a polar aprotic solvent which is inert under the conditions of the reaction, which may or may not be anhydrous and in general is at the boiling point of the solvent. The abovementioned polar aprotic solvents can be used in this reaction.

If desired, this reaction can also be carried out in the presence of an appropriate catalyst, such as, e.g., a phase transfer catalyst (e.g. a quaternary ammonium derivative).

The alkali metal, alkaline earth metal or ammonium salt of the compound (II) is prepared in a prior operation, optionally carried out in situ, by the action of an appropriate base (e.g. sodium hydroxide, potassium hydroxide or ammonia) or an alkali metal carbonate or alkali metal alcoholate (e.g. sodium methylate or sodium or potassium ethylate) on this compound (II).

After the reaction, whatever the process used, the compound formed is isolated from the reaction medium by any method which is known per se, such as, e.g., by distillation of the solvent, by crystallisation of the product in the reaction medium or by filtration, and, if necessary, this compound is purified by the usual methods, such as recrystallisation from an appropriate solvent or liquid chromatography over a column of silica or alumina.

The 2-cyano-imidazopyridine of the formula (II) which is the starting substance in the preparation process according to the invention can be prepared by the action of ammonia on the 2-trichloromethyl-imidazopyridine of the formula (IV):

(IV)

in which $Z_1$, $Z_2$, $Z_3$ and $Z_4$ have the same meaning as in formula (I), at a temperature of the order of 10° C.

The 2-trichloromethyl-imidazopyridine of the formula (III) is itself obtained by the action of methyl trichloroacetimidate of the formula (V)

$Cl_3C-C=NH$
         $|$
         $OCH_3$
(V)

on the 2,3-diaminopyridine of the formula (VI):

(VI)

in which $Z_1$, $Z_2$, $Z_3$ and $Z_4$ have the same meaning as in formula (I), in the presence of acetic acid.

The compounds of the formulae (III) and (IV) are included in the scope of the present invention as new chemical products which can be used, in particular, for carrying out the preparation process described above.

They have the general formula (VII)

(VII)

in which $Z_1$, $Z_2$, $Z_3$ and $Z_4$ have the same meaning as in formula (I) and U represents either the cyano radical or the trichloromethyl radical.

The examples below illustrate the invention, without, however, limiting it.

The structure of the compounds described in these examples have been confirmed by nuclear magnetic resonance spectrometry (NMR) and/or by infrared spectrometry.

EXAMPLE 1

Preparation of 3H-2-cyano-3-dimethylsulphamylimidazo[4,5-b]pyridine of the formula:

(No. 1A)

and of 1H-2-cyano-1-dimethylsulphamylimidazo[4,5-b]pyridine of the formula:

(No. 1B)

Anhydrous potassium carbonate (8.4 g) is added to a solution of 2-cyano-imidazo[4,5-b]pyridine (8 g) in acetonitrile (100 ml).

The mixture obtained is heated at the reflux temperature of acetonitrile for one hour and cooled to 30° C. and dimethylsulphamyl chloride (8.25 g=6.15 ml) is then added all at once.

The reaction mixture is then heated to the reflux temperature of acetonitrile and kept at this temperature for one hour.

The reaction mixture is subsequently heated and cooled and then filtered, and, finally, is concentrated to dryness under reduced pressure (about 20 millibar).

The solid residue obtained (13.5 g) is taken up in ethyl acetate (150 ml) and the mixture is chromatographed over a silica column.

Compound No. 1A (2.9 g), in the form of white crystals of melting point 166° C., and compound No. 1B (5.6 g), in the form of white crystals of melting point 150° C., are thus obtained.

The 2-cyano-imidazo[4,5-b]pyridine of the following formula:

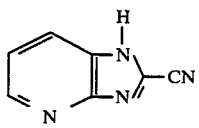

was prepared by the process described below:

2-Trichloromethyl-imidazo[4,5-b]pyridine (21.5 g) is added, in small portions, to 34% strength ammonia (250 ml), which is stirred vigorously and kept at about 10° C. After the addition, the reaction mixture is stirred for about one hour, the temperature being allowed to rise to the ambient temperature (20° to 25° C.). The reaction mixture is filtered over silica supercel and the filtrate is acidified to pH=6 with hydrochloric acid (200 ml) of density 1.19, the temperature being kept below 10° C. 2-Cyanoimidazo[4,5-b]pyridine (8 g in total) of melting point of about 200° C. is obtained by filtering off the precipitate, extracting the mother liquors with ethyl acetate and concentrating the extract. Purity: about 80%.

The 2-trichloromethyl-imidazo[4,5-b]pyridine of the formula:

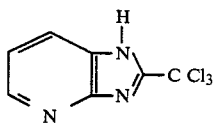

was prepared by the process described below:

Methyl trichloroacetimidate (32.8 g=22.75 ml) is added all at once to a solution of 2,3-diaminopyridine (19.7 g) in acetic acid (400 ml) and the reaction mixture is left to stand at the ambient temperature (20° to 25° C.) for 72 hours.

The reaction mixture obtained is then poured onto ice-water (1.5 liters). The crystalline precipitate is drained, washed with water and dried. 2-Trichloromethylimidazo[4,5-b]pyridine (21.15 g) of melting point 210° C. is thus obtained.

EXAMPLE 2

By working according to the method described in the preceding example, using appropriate starting substances, the compounds below were prepared:

No. 2A: 3H-6-Chloro-2-cyano-3-dimethylsulphamylimidazo[4,5-b]pyridine,
No. 2B: 1H-6-Chloro-2-cyano-1-dimethylsulphamylimidazo[4,5-b]pyridine,
No. 3A: 3H-2-Cyano-5,6-dichloro-3-dimethylsulphamylimidazo[4,5-b]pyridine, in admixture (65/35) with compound 3B
No. 3B: 1H-2-Cyano-5,6-dichloro-1-dimethylsulphamylimidazo[4,5-b]pyridine,
No. 4A: 3H-2-Cyano-3-dimethylsulphamyl-7-methylimidazo[4,5-b]pyridine,
No. 5A: 3H-6-Bromo-2-cyano-3-dimethylsulphamylimidazo[4,5-b]pyridine,
No. 5B: 1H-6-Bromo-2-cyano-1-dimethylsulphamylimidazo[4,5-b]pyridine,
No. 6A: 3H-2-Cyano-3-dimethylsulphamyl-6-methylimidazo[4,5-b]pyridine, and
No. 6B: 1H-2-Cyano-1-dimethylsulphamyl-6-methylimidazo[4,5-b]pyridine.

The formulae of these compounds and their melting points are shown in Table I at the end of the description.

EXAMPLE 3

Greenhouse tests on tomato blight

Tomato plants (*Lycopersicum esculentum*) of the Marmande variety are grown in pots. When these plants are one month old (5- or 6-leaf stage, 12 to 15 cm in height), they are treated by spraying with an aqueous suspension or solution of the substance to be tested, the suspension or solution having the desired concentration and containing 0.02% of a condensation product of sorbitan monooleate and 20 molecules of ethylene oxide. Each tomato plant receives about 5 ml of the solution or dispersion. The treatment is carried out on eight plants for each concentration of active ingredient to be tested. The plants used as controls are treated with a solution containing no active ingredient but containing 0.02% of the same condensate of sorbitan monooleate and ethylene oxide.

After drying for 4 hours, each plant is contaminated by spraying with an aqueous suspension of *Phytophthora infestans* spores, which are responsible for tomato blight, in an amount of about 1 ml/plant (i.e. about $2 \times 10^5$ spores per plant).

After this contamination, the tomato plants are incubated at about 20° C. in an atmosphere saturated in moisture for three days and then at about 17° C. under 70% to 80% relative humidity for four days.

Seven days after the contamination, the results obtained in the case of the plants treated with the active ingredient to be tested are compared with those obtained in the case of the plants used as controls, and the minimum inhibitory concentration causing 95 to 100% inhibition of the development of the fungus in question (MIC 95-100) is determined.

Under these conditions, it is found that, for the compounds or mixtures of compounds described in the preceding examples, this concentration was, respectively, as follows:

| Compound or mixture tested | MIC (95–100) *Phytophthora infestans* in mg/liter |
| --- | --- |
| 1B | 8 |
| 2A | 4 |
| 2B | 8 |
| 3A + 3B (65/35) | 1 |
| 3B | 1 |
| 4A | greater than 16 mg/litre |
| 5A | 8 |
| 5B | less than or equal to 2 mg/liter |

In this test, percentages of inhibition of the development of the fungus in question of between 20% and 90% were found:
at a dose of 500 mg/liter for compounds Nos. 1A and 6A, and
at a dose of 8 mg/liter for compound 6B.

EXAMPLE 4

Greenhouse test on blue mould of tobacco

The procedure followed is as in the preceding example, except that the plants are tobacco plants (*Nicotiana tabacum*) of the Samson variety and that these plants are contaminated with spores of *Peronospora tabaci*, which are responsible for blue mould of tobacco.

Under these conditions, it was found that, for the compounds or mixtures of compounds described in the preceding examples, the minimum inhibitory concentrations causing 95 to 100% inhibition of the fungus in question (MIC 95–100) are, respectively, the following:

| Compound or mixture tested | MIC (95-100) *Peronospora tabaci* in mg/liter |
| --- | --- |
| 1B | 16 |
| 2A | less than or equal to 2 |
| 2B | 4 |
| 5B | 8 |
| 6A | less than or equal to 4 |

In this test, percentages of inhibition of the development of the fungus in question of between 20% and 90% were found:
at a dose of 500 mg/liter for compounds Nos. 1A and 6B, and
at a dose of 8 mg/liter for compounds Nos. 3A, 3B and 5A.

Examples Nos. 3 and 4 described above illustrate the good fungicidal activity of the compounds according to the invention.

The compounds according to the invention are advantageously used as fungicides in the agricultural sector. They have a contact action and a systemic action and can be used preventively and/or curatively for combating various phytopathogenic fungi, such as, e.g., numerous phycomycetes and basidiomycetes.

For their use in practice, the compounds according to the invention are not generally employed by themselves. Most frequently, they are used in compositions which generally comprise, in addition to the active ingredient, an inert carrier (or diluent) and/or a surface-active agent which are compatible with the active ingredient.

These compositions also form part of the present invention. They usually contain from 0.001 to 95% by weight of active ingredient. They generally contain between 0% and 20% by weight of surface-active agent.

In the present account, the term "carrier" denotes an organic or inorganic, natural or synthetic material with which the active ingredient is combined in order to facilitate its application to the plant, to seeds or to the soil. This carrier is therefore generally inert and it must be acceptable in agriculture, in particular on the plant treated. The carrier can be solid (clays, natural or synthetic silicates, silica, chalks, resins, waxes, solid fertilisers and the like) or liquid (water, alcohols, ketones, petroleum fractions, aromatic or paraffinic hydrocarbons, chlorohydrocarbons, liquefied gases and the like).

The surface-active agent can be an emulsifying, dispersing or wetting agent of the ionic or non-ionic type. Examples which may be mentioned are polyacrylic acid salts; lignosulphonic acid salts and phenolsulphonic or naphthalenesulphonic acid salts; polycondensates of ethylene oxide with fatty alcohols, fatty acids, fatty amines or substituted phenols (in particular alkylphenols, arylphenols or styrylphenol); salts of sulphosuccinic acid esters; taurine derivatives (in particular alkyltaurates); and phosphoric acid esters of condensates of ethylene oxide with alcohols or phenols. The presence of at least one surface-active agent is generally essential, especially if the inert carrier is not soluble in water and if the vehicle of application is water.

The compositions used in the invention can be in a fairly wide variety of solid or liquid forms.

As forms of solid compositions there may be mentioned dusting powders (with an active ingredient content which can range up to 100%).

As forms of liquid compositions or compositions which are to be made up into liquid compositions on application, there may be mentioned solutions, in particular water-soluble concentrates, emulsifiable concentrates, emulsions, suspension concentrates, aerosols, wettable powders (or spraying powders) and pastes.

The emulsifiable or soluble concentrates most frequently comprise 10 to 80% of active ingredient, and the emulsions or solutions which are ready for application contain 0.001 to 20% of active ingredient. In addition to the solvent, and where necessary, the emulsifiable concentrates can contain a suitable co-solvent and 2 to 20% of suitable additives, such as stabilisers, surface-active agents, in particular emulsifiers, penetrating agents, corrosion inhibitors, dyestuffs and adhesives.

Starting from these concentrates, emulsions of any desired concentration, which are particularly suitable for application to the crops, can be obtained by dilution with water.

The suspension concentrates, which can also be applied by spraying, are prepared so as to give a stable fluid product which does not form a deposit, and they usually contain from 10 to 75% of active ingredients, from 0.5 to 15% of surface-active agents, from 0.1 to 10% of thixotropic agents, from 0 to 10% of suitable additives, such as anti-foam agents, corrosion inhibitors, stabilisers, penetrating agents and adhesives, and, as the carrier, water or an organic liquid in which the active ingredient is sparingly soluble or insoluble: certain organic solids or mineral salts can be dissolved in the carrier in order to assist in preventing sedimentation or to act as anti-freeze agents for the water.

The wettable powders (or spraying powder) are usually prepared so as to contain 20 to 95% of active ingredients, and they usually contain, in addition to the solid carrier, from 0 to 5% of a wetting agent, from 3 to 10% of a dispersing agent and, where necessary, from 0 to 10% of one or more stabilisers and/or other additives, such as penetrating agents, adhesives, anti-caking agents, dyestuffs and the like.

By way of example, the composition of a 50% strength wettable powder is as follows:

| | |
| --- | --- |
| active ingredient | 50% |
| ethylene oxide/fatty alcohol condensate | 2.5% |

|   |   |
|---|---|
| (wetting agent) | |
| ethylene oxide/styrylphenol condensate (dispersing agent) | 5% |
| chalk (inert carrier) | 42.5% |

Another example of a wettable powder has the following composition:

|   |   |
|---|---|
| active ingredient | 90% |
| ethylene oxide/fatty alcohol condensate (wetting agent) | 4% |
| ethylene oxide/styrylphenol condensate (dispersing agent) | 6% |

Another example of a 50% strength wettable powder has the following composition:

|   |   |
|---|---|
| active ingredient | 50% |
| mixture of anionic and non-ionic surface-active agents (wetting agent) | 2.5% |
| neutral sodium lignosulphonate (dispersing agent) | 5% |
| kaolin clay (inert carrier) | 42.5% |

To obtain these spraying powders or wettable powders, the active ingredient is intimately mixed with the additional substances in suitable mixers and the mixture is ground in mills or other suitable grinders. This gives spraying powders of advantageous wettability and suspendibility; they can be suspended in water at any desired concentration and this suspension can be used very advantageously, in particular for application to the leaves of the plants.

As already stated, the aqueous dispersions and emulsions, e.g. compositions obtained by diluting, with water, a wettable powder or an emulsifiable concentrate according to the invention, are included within the general scope of the compositions which can be used in the present invention. The emulsions can be of the water-in-oil or oil-in-water type and they can have a thick consistency such as that of a "mayonnaise".

The granules, which are intended to be placed on the soil, are usually prepared so as to have dimensions of between 0.1 and 2 mm, and they can be manufactured by agglomeration or impregnation. In general, the granules contain 0.5 to 25% of active ingredient and 0 to 10% of additives, such as stabilisers, slow release modifiers, binders and solvents.

The compounds of the formula (II) can also be used in the form of dusting powders; thus, it is possible to use a composition comprising 50 g of active ingredient and 950 g of talc; it is also possible to use a composition comprising 20 g of active ingredient, 10 g of finely divided silica and 970 g of talc; these constituents are mixed and ground and the mixture is applied by dusting.

The invention also relates to a process for treating plants against phytopathogenic fungi.

This process comprises applying to these plants an effective amount of a compound according to one of the formulae (I), I a and I b. The term "effective amount" is understood as meaning a sufficient amount to enable the fungi present on these plants to be controlled and destroyed. However, the doses used can vary within wide limits, according to the fungus to be combated, the type of crop, the climatic conditions and the compound used.

In practice, doses of from 5 g/hectoliter to 100 g/hectoliter, substantially corresponding to doses of active ingredient per hectare of about 50 g/ha to 1,000 g/ha, generally give good results.

TABLE I

| Compound n° | FORMULA | Melting Point (°C.) |
|---|---|---|
| 2A | 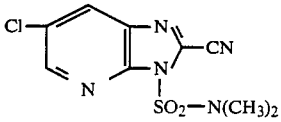 | 196 |
| 2B | 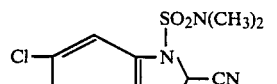 | 172 |
| 3A | 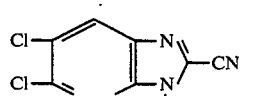 | Mixture 3A + 3B (65/35) 195–200 |
| 3B | 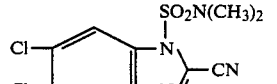 | 215–220 (with decomposition) |
| 4A | 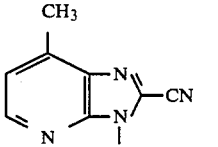 | 180 |
| 5A | 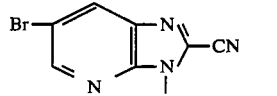 | 172 |
| 5B | 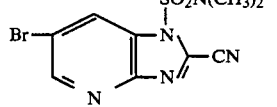 | 210 |
| 6A | 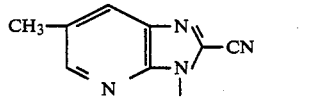 | 190 |
| 6B | 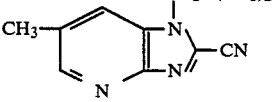 | 190 |

We claim:

1. A compound having the formula (I):

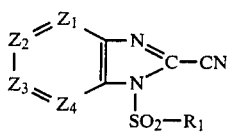

in which $R_1$ is lower alkyl, halogen substituted lower alkyl bearing at least one halogen substituent, lower cycloalkyl, halogen substituted lower cycloalkyl bearing at least one halogen substituent, amino, lower alkylamino or di-lower alkylamino, one of the groups $Z_1$, $Z_2$, $Z_3$ and $Z_4$ is a nitrogen atom and the others, which may be the same or different, are independently CH or CR, wherein R is halogen, lower alkyl, halogen substituted lower alkyl bearing at least one halogen substituent, lower alkoxy, halogen substituted lower alkoxy bearing at least one halogen substituent, lower alkylthio, halogen substituted lower alkylthio bearing at least one halogen substituent, nitro or cyano.

2. A compound as defined by claim 1, wherein $Z_1$ is a nitrogen atom.

3. A compound as defined by claim 1, wherein $Z_2$ is a nitrogen atom.

4. A compound as defined by claim 1, wherein $Z_3$ is a nitrogen atom.

5. A compound as defined by claim 1, wherein $Z_4$ is a nitrogen atom.

6. A compound as defined by claim 1 wherein $R_1$ is lower alkyl.

7. A compound as defined by claim 1 wherein $R_1$ is lower alkyl bearing at least one halogen substituent.

8. A compound as defined by claim 1 wherein $R_1$ is lower cycloalkyl.

9. A compound as defined by claim 1 wherein $R_1$ is halogen substituted lower cycloalkyl bearing at least one halogen substituent.

10. A compound as defined by claim 1 wherein $R_1$ is amino.

11. A compound as defined by claim 1 wherein $R_1$ is mono-lower alkylamino.

12. A compound as defined by claim 1 wherein $R_1$ is di-lower alkylamino.

13. A compound as defined by claim 1 wherein $Z_1$ is nitrogen and $Z_2$, $Z_3$ and $Z_4$ are each independently selected from CH and CR groups wherein R is halogen or lower alkyl.

14. A compound as defined by claim 13 wherein $R_1$ is a di-lower alkylamino.

15. A compound as defined by claim 14 having the structure:

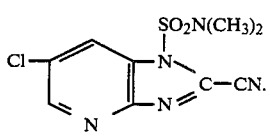

(2B)

16. A compound as defined by claim 14 having the structure:

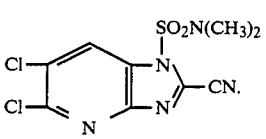

(3B)

17. A compound as defined by claim 14 having the structure:

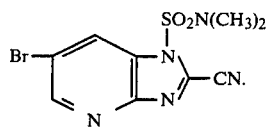

(5B)

18. A compound as defined by claim 14 having the structure:

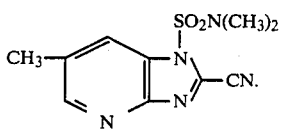

(6B)

19. A compound as defined by claim 1 wherein $Z_4$ is nitrogen and $Z_1$, $Z_2$ and $Z_3$ are each independently selected from CH and CR groups wherein R is halogen or lower alkyl.

20. A compound defined by claim 19 wherein $R_1$ is di-lower alkylamino.

21. The compound as defined by claim 20 having the structure:

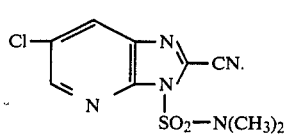

(2A)

22. The compound as defined by claim 20 having the structure:

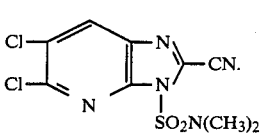

(3A)

23. The compound as defined by claim 20 having the stucture:

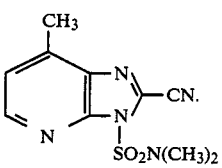

(4A)

24. The compound as defined by claim 20 having the structure:

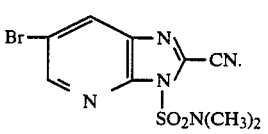

(5A)

25. The compound as defined by claim 20 having the following structure:

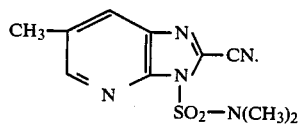 (6A)

26. A fungicidal composition comprising a fungicidally effective amount of a fungicidally effective compound as defined by claim 1 and an agriculturally acceptable inert carrier or diluent.

27. The fungicidal composition as defined by claim 26 further comprising a surface-active agent compatible with the active ingredient.

28. The fungicidal composition as defined by claim 27 comprising from 0.001% to 95% by weight of said fungicidally effective compound.

29. The fungicidal composition as defined by claim 26, formulated as an emulsifiable concentrate.

30. A fungicidal composition comprising a fungicidally effective amount of an admixture of more than one fungicidally effective compound as defined by claim 1 and an agriculturally acceptable inert carrier or diluent.

31. A method for combatting phytopathogenic fungi, comprising applying to the locus of such fungi, a fungicidally-effective amount of a compound as defined by claim 1.

32. A method for combatting phytopathogenic fungi, comprising applying to the locus of such fungi, a fungicidally-effective amount of a compound as defined by claim 13.

33. A method for combatting phytophathogenic fungi, comprising applying to the locus of such fungi, a fungicidally-effective amount of a compound as defined by claim 20.

34. A method for combatting phytopathogenic fungi, comprising applying to the locus of such fungi, a fungicidally-effective amount of the composition of claim 26.

35. A method for combatting phytopathogenic fungi, comprising applying to the locus of such fungi, a fungicidally-effective amount of the composition of claim 27.

36. A method for combatting phytopathogenic fungi, comprising applying to the locus of such fungi, a fungicidally-effective amount of the composition of claim 28.

37. A method for combatting phytopathogenic fungi, comprising applying to the locus of such fungi, a fungicidally-effective amount of the composition of claim 29.

* * * * *